United States Patent [19]

Nagoshi et al.

[11] Patent Number: 5,759,848
[45] Date of Patent: Jun. 2, 1998

[54] BIOLOGICAL INDICATOR

[75] Inventors: Jinko Nagoshi, Tonami; Yuzo Ueda, Osawano-machi; Naotake Eidai, Toyama; Yukio Wakabayashi, Fuchu-machi; Toshihiro Nogami, Toyama, all of Japan

[73] Assignee: Fujiyakuhin Co., Ltd., Oomiya, Japan

[21] Appl. No.: 796,750

[22] Filed: Feb. 6, 1997

[30] Foreign Application Priority Data

May 14, 1996 [JP] Japan .................. 7-118747

[51] Int. Cl.⁶ .................................. C12M 3/00
[52] U.S. Cl. .................. 435/287.1; 435/287.4; 435/287.6; 435/287.7
[58] Field of Search .................. 435/287.1, 287.4, 435/287.6, 287.7

[56] References Cited

U.S. PATENT DOCUMENTS

| | | | |
|---|---|---|---|
| 4,416,984 | 11/1983 | Wheeler | 435/287.4 |
| 4,528,268 | 7/1985 | Andersen et al. | 435/287.4 |
| 4,743,537 | 5/1988 | McCormick et al. | 435/287.6 |
| 5,340,741 | 8/1994 | Lemonnier | 435/288.1 |

*Primary Examiner*—David A. Redding
*Attorney, Agent, or Firm*—Oblon, Spivak, McClelland, Maier & Neustadt, P.C.

[57] ABSTRACT

Described is a biological indicator which comprises an indicator microorganism and a film which allows the permeation of a sterilizing gas but does not allow the permeation of the microorganism, said microorganism having been wrapped with the film.

1 Claim, No Drawings

BIOLOGICAL INDICATOR

BACKGROUND OF THE INVENTION

1. Field of the Invention

This invention relates to a biological indicator used for the verification of the effects of disinfection, fumigation or sterilization of microorganisms by using high pressure steam, a sterilizing gas, hydrogen peroxide, ozone, electron beam, gamma rays or the like.

2. Description of the Related Art

Microorganisms are generally classified into two groups, that is, bacteria and fungi and each group has a fixed shape and size. These microorganisms exhibit pathogenicity when mixed in a pharmaceutical, cosmetics or food, thereby exerting serious influences on the quality of the product, for example, deterioration in its quality or impairment of its flavor. When microorganisms or their dead bodies are mixed in an injection, on the other hand, they have serious influences on the patient to whom the injection has been administered, for example, by causing infectious diseases.

With a view to maintaining the quality of a pharmaceutical, it is therefore very important to remove such microorganisms from its production environment and to take measures against the contamination of the microorganisms into it. For the above purposes, it is inevitable to perform disinfection, fumigation or sterilization of the production environment, production equipment, materials, working clothes and the like. In addition, in the medical job site, it is also inevitable to perform disinfection, fumigation or sterilization of an operating room, tools and materials for operation, an operating gown and operating clothes in order to prevent hospital infection, thereby maintaining the medical safety.

To verify that the disinfection, fumigation or sterilization work has accomplished its object, it is the common practice to investigate the dying degree of the microorganisms, whether the disinfection, fumigation or sterilization has been performed with certainty, using living microorganisms as an indicator.

Examples of the microorganisms used generally for a biological indicator include thermophilic bacteria, chemical-resistant bacteria, poisonous-gas-resistant bacteria and radiation-resistant bacteria, more specifically, *Bacillus subtilis* var. *niger*, *Bacillus stearothermophilus* or *Bacillus pumilus*. As the biological indicator, a carrier onto which some of these microorganisms have been adhered in a viable count of $10^2$–$10^8$ is used. Although such active microorganisms are widely used as a biological indicator (BI), there is a danger that owing to incomplete wrapping, they leak from the wrapping or pass through the wrapping, scatter around and contrary to the original purpose, become a cause of bacterial pollution. It is the present situation that particularly in the case where containers, clothes or the like are sterilized by using a poisonous gas, hydrogen peroxide or ozone or where a production site of pharmaceuticals, an operating room or the like is sterilized by fumigation, the effects of the above-described biological indicator cannot be verified without using an excess amount of a poisonous gas, hydrogen peroxide or ozone, because the wrapping for tightly sealing of the above-described biological indicator markedly prevents the gas permeability. An excess amount of the poisonous gas, hydrogen peroxide or ozone increases not only an adverse effect on the human body, environment, equipment and the like but also a danger of causing a fire. Accordingly, there is a strong demand for the establishment of a method for carrying out disinfection, fumigation or sterilization at more appropriate concentration of the above-described sterilizing gas.

SUMMARY OF THE INVENTION

An object of the present invention is therefore to provide a biological indicator which makes it possible to verify the sterilization condition effectively and safely without using an excess amount of a sterilizing gas.

With a view to attaining the above object, the present inventors have carried out an extensive investigation. As a result, it has been found that by employing, as a wrapping material of indicator microorganisms, a specific film which permits the permeation of a gas but does not permit the permeation of the microorganisms, the microorganisms do not leak and scatter from the film, while the sterilizing gas sterilizes the indicator microorganisms at the same concentration as in the outside of the film. Thus, the sterilization condition can be verified safely and effectively, leading to the completion of the present invention.

The present invention, that is to say, provides a characteristic biological indicator which comprises an indicator microorganism wrapped in a specific film permitting the permeation of a sterilizing gas without permitting the permeation of the microorganism.

Accordingly, the present invention makes it possible to provide a biological indicator which allows the effective permeation of ozone, hydrogen peroxide gas or poisonous gas and causes neither leakage nor permeation of the microorganisms from the wrapping film and which is used for the confirmation of the effects of disinfection, fumigation or sterilization. As a result, the concentration of ozone, hydrogen peroxide gas or poisonous gas can be suppressed to the minimum, whereby sterilization can be verified effectively and safely without scattering the microorganisms around the place to be verified.

DETAILED DESCRIPTION OF THE PREFERRED EMBODIMENTS

No other particular limitation than the permeability of a sterilizing gas and no permeability of microorganism, is imposed on the film to be used for the biological indicator of the present invention insofar. Those having pores through which not microorganisms but a sterilizing gas is permeable are preferred. It is preferred that the pore size of the film is 0.01 μm to 0.5 μm, with 0.1 μm to 0.3 μm being particularly preferred. In consideration of the necessity of the effective permeation of a sterilizing gas, it is preferred that the gas permeability of the film is at least 1000 ml/cm²/bar, with at least 2000 ml/cm²/bar being particularly preferred. Furthermore, from the viewpoint of the gas permeability, the porosity of the film is preferably 50% or higher, with 70% or higher being particularly preferred.

Incidentally, the gas permeability can be determined by calculating the gas permeable amount per hour and per area after measuring the amount of the gas permeated through a film under a fixed pressure. The porosity, on the other hand, can be determined in accordance with the following equation by using the difference between the weights of the film before and after impregnation with a liquid.

$$\text{Porosity (\%)} = \frac{W_2 - W_1}{C \cdot V} \times 100$$

wherein:

$W_1$: weight of the film $W_2$: weight of the film after impregnated with a liquid V: volume of the film, and C: specific gravity of the liquid No particular limitation is imposed on the material of the film insofar other than heat-, chemical- and radiation-resistance without a decrease of the killing effects of ozone, hydrogen peroxide or poisonous gas to microorganisms. Examples of the material include cellulose ester, cellulose acetate, cellulose nitrate, polyamide, polyvinylidene fluoride, polytetrafluoroethylene, polycarbonate, polyethylene, nylon and polypropylene.

The biological indicator according to the present invention can be obtained by having an indicator microorganism borne on a carrier and then packing it with the above-described film. Here, examples of the usable indicator microorganism generally include thermophilic bacteria, chemical-resistant bacteria, poisonous-gas-resistant bacteria and radiation-resistant bacteria, for example, Bacillus subtilis var. niger, Bacillus stearothermophilus or bacillus pumilus. As the carrier, a filter paper is generally employed. Porous synthetic resins and ceramics can also be used. The viable count of the microorganisms which have been borne on the carrier may be $10^2$–$10^8$.

For the purpose of transportation or preservation, the biological indicator according to the present invention may be contained in a container or the like which does not allow the permeation of both a gas and microorganisms.

The verification of the sterilizing effects using the biological indicator according to the present invention is carried out in a conventional manner. Described specifically, the biological indicator of the present invention is positioned on the place to be sterilized and sterilization is effected using an ozone gas, ethylene oxide gas, hydrogen peroxide gas or formalin gas. The indicator microorganism is then taken out from the wrapping and incubated on a nutrient medium, followed by the observation of the presence or absence of the proliferation of the microorganisms.

The present invention will hereinafter be described in more specifically by the following examples. It should however be borne in mind that the present invention will not be limited to or by the following examples.

EXAMPLE 1

A filter paper to which Bacillus subtilis var. niger had been adhered in a viable count of $10^6$ as an indicator microorganism was wrapped with a polyvinylidene fluoride film having a pore size of 0.22 µm, gas permeability of 4000 ml/cm²/min/bar and porosity of 75% by the heat sealing method, whereby a biological indicator was prepared.

Test 1

Each of the biological indicator obtained in Example 1, a biological indicator (S) which was Example 1 without wrapping, and two commercially available biological indicators (A) and (B) to which Bacillus subtilis var. niger had been adhered in a viable count of $10^6$, was exposed to an ozone gas and ethylene oxide gas respectively under the conditions described below. Thereafter, each of the indicators was taken out from the wrapping except the indicator (S) and the sterilization effects were confirmed using a soybean-casein-digest agar (SCD) medium.

The results are shown in Tables 1 and 2.

TABLE 1

| Exposure Test to Ozone | | | | |
|---|---|---|---|---|
| | Example 1 | (S) | (A) | (B) |
| 300 ppm | Positive | Positive | Positive | Positive |
| 500 ppm | Negative | Negative | Positive | Positive |
| 700 ppm | Negative | Negative | Positive | Positive |
| 900 ppm | Negative | Negative | Positive | Negative |
| 1200 ppm | Negative | Negative | Negative | Negative |

Exposure conditions: at 20° C. for 120 min.

TABLE 2

| Exposure Test to Ethylene Oxide Gas | | | | |
|---|---|---|---|---|
| | Example 1 | (S) | (A) | (B) |
| 30 min | Positive | Positive | Positive | Positive |
| 60 min | Negative | Negative | Positive | Positive |
| 90 min | Negative | Negative | Positive | Positive |
| 120 min | Negative | Negative | Negative | Negative |

Exposure conditions: at 60° C., 75%, 640 mg/l

Test 2

Each of the biological indicator obtained in Example 1, a biological indicator (S) which was Example 1 without wrapping, and two commercially available biological indicators (A) and (B) to which Bacillus subtilis var. niger had been adhered in a viable count of $10^6$ were subjected to an incubation test on an SCD medium without being taken out from the wrapping except the indicator (B).

The results are shown in Table 3.

TABLE 3

| Leakage and Permeation Test | | | | |
|---|---|---|---|---|
| | Example 1 | (S) | (A) | (B) |
| Results | Negative | Positive | Positive | Positive |

It has been confirmed that the biological indicator of Example 1 has good gas permeability and causes neither leakage nor permeation of the microorganisms from the wrapping.

EXAMPLE 2

A filter paper to which Bacillus subtilis var. niger had been adhered in a viable count of $10^6$ as an indicator microorganism was wrapped with a polytetrafluoroethylene film having a pore size of 0.2 µm, gas permeability of 4000 ml/cm²/min/bar and porosity of 85% by the heat sealing method, whereby a biological indicator was prepared.

Test 3

Each of the biological indicator obtained in Example 2, a biological indicator (S) which was Example 2 without wrapping, and two commercially available biological indicators (A) and (B) to which Bacillus subtilis var. niger had been adhered in a viable count of $10^6$, were exposed to a hydrogen peroxide gas and formalin gas, respectively, under the conditions described below. Thereafter, each of the indicators was taken out from the wrapping except the indicator (S) and the sterilization effects were confirmed using a soybean-casein-digest agar (SCD) medium.

The results are shown in Tables 4 and 5.

TABLE 4

| Exposure Test to Hydrogen Peroxide Gas | | | | |
|---|---|---|---|---|
| | Example 2 | (S) | (A) | (B) |
| 500 ppm | Positive | Positive | Positive | Positive |
| 1000 ppm | Negative | Negative | Positive | Positive |
| 1500 ppm | Negative | Negative | Positive | Positive |
| 2000 ppm | Negative | Negative | Positive | Negative |
| 3200 ppm | Negative | Negative | Negative | Negative |

Exposure conditions: at 20° C. for 120 min.

TABLE 5

| Exposure Test to Formalin Gas | | | | |
|---|---|---|---|---|
| | Example 2 | (S) | (A) | (B) |
| 1000 ppm | Positive | Positive | Positive | Positive |
| 2000 ppm | Negative | Negative | Positive | Positive |
| 3000 ppm | Negative | Negative | Positive | Positive |
| 4000 ppm | Negative | Negative | Negative | Negative |

Exposure conditions: at 20° C., 70%

Test 4

Each of the biological indicator obtained in Example 2, a biological indicator (S) which was Example 2 without wrapping, and two commercially available biological indicators (A) and (B) to which *Bacillus subtilis var. niger* had been adhered in a viable count of $10^6$, was subjected to an incubation test on an SCD medium without being taken out from the wrapping.

The results are shown in Table 6.

TABLE 6

| Leakage and Permeation Test | | | | |
|---|---|---|---|---|
| | Example 2 | (S) | (A) | (B) |
| Results | Negative | Positive | Positive | Positive |

It has been confirmed that the biological indicator of Example 2 has good gas permeability and causes neither leakage nor permeation of the microorganisms from the wrapping.

What is claimed is:

1. A biological indicator, which consists essentially of an indicator microorganism and a film which allows the permeation of a sterilizing gas but does not allow the permeation of the microorganism, said microorganism having been substantially wrapped with the film alone, and wherein the film has pores of 0.01 μm to 0.5 μm in pore size and wherein the film has gas permeability of at least 1000 ml/cm²/min/bar.

* * * * *

UNITED STATES PATENT AND TRADEMARK OFFICE
CERTIFICATE OF CORRECTION

PATENT NO. : 5,759,848
DATED : JUNE 2, 1998
INVENTOR(S) : JINKO NAGOSHI ET AL.

It is certified that error appears in the above-identified patent and that said Letters Patent is hereby corrected as shown below:

On the title page, delete Item [30] in its entirety and replace with
--[30] Foreign Application Priority Data
May 14, 1996 [JP]    Japan   8-118747--

Signed and Sealed this

Twenty-sixth Day of January, 1999

Attest:

Attesting Officer

*Acting Commissioner of Patents and Trademarks*